United States Patent [19]

Bourzat et al.

[11] Patent Number: 5,102,890
[45] Date of Patent: Apr. 7, 1992

[54] PYRROLE DERIVATIVES, THEIR PREPARATION AND PHARMACEUTICAL COMPOSITIONS WHICH CONTAIN THEM

[75] Inventors: Jean-Dominique Bourzat, Paris; Marc Capet, Thiais; Claude Cotrel, Paris, all of France; Richard Labaudiniere, Bruehl, Fed. Rep. of Germany; Philippe Pitchen, Brentwood, United Kingdom; Gerard Roussel, Soisy S/Seine, France

[73] Assignee: Rhone-Poulenc Sante, Antony, France

[21] Appl. No.: 402,457

[22] Filed: Sep. 5, 1989

[51] Int. Cl.$^5$ .................. A61K 31/535; C07D 215/38; C07D 471/02; C07D 471/00

[52] U.S. Cl. .................................... 514/299; 546/159; 546/157; 546/122; 546/270; 546/167; 544/350; 544/127; 544/128; 544/131; 544/362; 544/363; 544/364; 548/482; 514/234.5; 514/314; 514/235.2; 514/253

[58] Field of Search ............... 546/159, 157, 122, 270, 546/167; 544/350; 548/482; 514/299, 314

[56] References Cited

U.S. PATENT DOCUMENTS 3,847,921  11/1974  Cotrel et al. ..................... 546/159

FOREIGN PATENT DOCUMENTS 174858   3/1986  European Pat. Off. .
2101081  3/1972  France ............................. 546/159
2115045  7/1972  France ............................. 546/159

OTHER PUBLICATIONS

Copy of European Search Report dated Sep. 17, 1987.
Liebigs Annalen Der Chemie, 1985, pp. 1679–1691, DE; L. Somogyi: "Isoindoline derivatives of opianic acid".

Primary Examiner—David B. Springer
Assistant Examiner—Robert C. Whittenbaugh
Attorney, Agent, or Firm—Morgan & Finnegan

[57] ABSTRACT

This invention relates to pyrrole derivatives of formula:

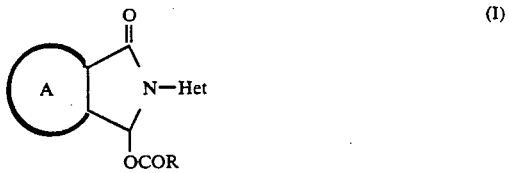

in which A forms with the pyrrole ring an isoindoline, 6,7-dihydro-5H-pyrrolo[3,4-b]pyrazine, 2,3,6,7-tetrahydro-5H-[1,4]oxathiino[2,3-c]pyrrole or 2,3,6,7-tetrahydro-5H-[1,4]dithiino[2,3-c]pyrrole ring-system and Het is naphthyridinyl, pyridyl or quinolyl which is unsubstituted or substituted with halogen, (1 to 4 C) alkyl, (1 to 4 C) alkyloxy, (1 to 4 C) alkylthio or $CF_3$ and R=(3 to 10 C) straight- or branched-chain alkenyl or alkyl which is unsubstituted or substituted with alkyloxy, alkylthio, (3 to 6 C) cycloalkyl, $NH_2$, alkylamino, dialkylamino, alkylcarbonylamino, (in which the amino portion is optionally substituted with alkyl), 1- or 2-piperazinyl, piperidyl, piperidino, morpholino, pyrrolidinyl, 1-azetidinyl, carbamoyl, alkylcarbamoyl, dialkylcarbamoyl, (1-piperazinyl)carbonyl, piperidinocarbonyl, (1-pyrrolidinyl)carbonyl, phenyl, pyridyl, 1-imidazolyl, or alternatively R=2- or 3-pyrrolidinyl, 2-, 3- or 4-piperidyl, on the understanding that the alkyl radicals are straight- or branched-chain radicals and contain, except where specifically stated, 1 to 10 C, and that the piperazinyl, piperidino, piperidyl, pyrrolidinyl and azetidinyl radicals can be unsubstituted or substituted at any position with alkyl, alkylcarbonyl, benzyl or hydroxyalkyl, or can alternatively form a lactam group with the nitrogen atom of the ring, and, where they exist, their pharmaceutically acceptable salts and optical isomers, are useful as anxiolytics.

9 Claims, No Drawings

PYRROLE DERIVATIVES, THEIR PREPARATION AND PHARMACEUTICAL COMPOSITIONS WHICH CONTAIN THEM

DESCRIPTION OF THE INVENTION

The present invention provides new pyrrole derivatives of the general formula:

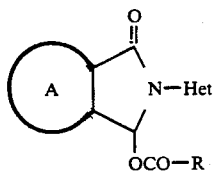
(I)

in which A forms with the pyrrole ring an isoindoline, 6,7-dihydro-5H-pyrrolo[3,4-b]pyrazine, 2,3,6,7-tetrahydro-5H-[1,4]oxathiino[2,3-c]pyrrole or 2,3,6,7-tetrahydro-5H-[1,4]-dithiino[2,3-c]pyrrole ring-system, Het denotes a naphthyridinyl, pyridyl or quinolyl radical which is un-substituted or substituted with a halogen atom or a (1 to 4 C) alkyl, (1 to 4 C) alkyloxy, (1 to 4 C) alkylthio or trifluoromethyl radical and R denotes a straight- or branched-chain alkenyl radical containing 3 to 10 carbon atoms or R denotes an alkyl radical which is unsubstituted or substituted by alkyloxy, alkythio, cycloalkyl of 3 to 6 carbon atoms, amino, alkylamino, dialkylamino, alkylcarbonylamino (in which the amino portion can optionally be substituted by alkyl), or 1- or 2-piperazinyl, piperidyl, piperidino, morpholino, pyrrolidinyl, 1-azetidinyl, carbamoyl, alkylcarbamoyl, dialkylcarbamol, (1-piperazinyl)-carbonyl, piperidinocarbonyl, (1-pyrrolidinyl)carbonyl, phenyl, pyridyl or 1-imidazolyl, or R denotes 2- or 3-pyrrolidinyl or 2-, or 4-piperidyl, the aforesaid alkyl radicals having a straight- or branched-chain and containing, except where specifically stated, 1 to 10 carbon atoms each, and the said piperazinyl, piperidino, piperidyl, pyrrolidinyl and azetidinyl radicals being unsubstituted or substituted at any position by alkyl, alkylcarbonyl, benzyl or hydroxyalkyl, or form a lactam group with the nitrogen atom of the ring, and, where they exist, their pharmaceuutically acceptable salts and the optical isomers of the pyrrole derivatives of formula (I).

According to a feature of the invention, the pyrrole derivatives of formula (I) in which Het is defined as above, but is not 1,8-naphthyridin-2-yl substituted at the 7-position by alkyloxy or alkylthio, and the other symbols are as defined above, are prepared by the action of an acid of formula:

R—COOH (II)

or an alkali metal salt of this acid, in which R is as defined above, on a compound of formula:

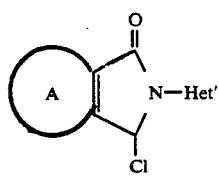
(III)

in which Het' has the meanings given above for Het, but is not 1,8-naphthyridin-2-yl substituted at the 7-position by alkyloxy or alkylthio, and A is as defined above.

The reaction is generally performed in the presence of a condensing agent, such as 1,8-diazabicyclo[5.4.0]-undec-7-ene or 1,5-diazabicyclo[5.3.0]non-5-ene, or a quaternary ammonium hydroxide, such as triethylbenzyl-ammonium hydroxide, in an organic solvent such as dimethylformamide at a temperature of between 20° and 100° C., or, when the alkali metal salt of the acid is used, in dimethylformamide at a temperature of 20° C.

The products of formula (III) may be prepared by chlorination of a compound of formula:

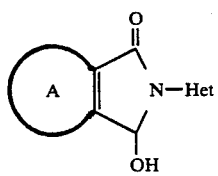
(IV)

in which A and Het are as defined above.

The reaction is generally performed in the presence of a chlorinating agent such as sulphinyl chloride or phosphorus oxychloride, in the presence of catalytic amounts of dimethylformamide, at a temperature between 20° C. and the reflux temperature of the reaction mixture, or of any other reagent known to those skilled in the art which enables a hydroxy radical to be converted into a chloro radical without affecting the remainder of the molecule.

The products of general formula (IV) may be prepared by application or adaptation of the methods described in Belgian Patent Nos. 815,019 or 835,325.

According to a further feature of the invention, the products of general formula (I) may also be prepared by the action of a compound of formula:

RCO—X (V)

in which R is as defined above and X denotes a halogen atom such as a chlorine atom, or alternatively denotes an active residue such as a 1-imidazolyl radical or a radical R"CO—O— in which R" denotes an alkyl radical, on a derivative of general formula (IV) as defined above.

The reaction is generally performed in an organic solvent such as chloroform or methylene chloride, or an ether such as tetrahydrofuran or dioxane, or alternatively in dimethylformamide at a temperature between 0° C. and the refluxing temperature of the reaction mixture, in the presence of a base such as sodium hydride or an acceptor for acid such as triethylamine or pyridine.

According to yet a further feature of the invention, the products of general formula (I) may also be prepared by the action of an alkali metal salt of an acid of general formula (II) on a product of general formula:

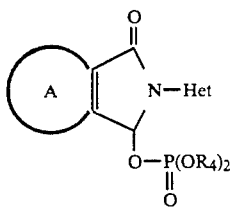

in which R₄ denotes a straight- or branched-chain alkyl radical containing 1 to 4 carbon atoms or a phenyl radical and A and Het are defined as above.

The reaction is generally performed in an organic solvent such as dimethylformamide at a temperature of between 0° and 25° C.

The products of general formula (VI) may be prepared by the action of a product of general formula:

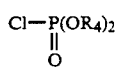

in which R₄ denotes a straight- or branched-chain alkyl radical containing 1 to 4 carbon atoms or a phenyl radical, on a product of general formula (IV) in which Het and A are defined as above.

The reaction is generally performed in an organic solvent such as dimethylformamide, in the presence of a base such as an alkali metal hydride, e.g. sodium hydride at a temperature of between −5° and +25° C.

It is not necessary to isolate the product of general formula (VI) in order to carry out the process according to the invention. It is sufficient to perform the condensation of the products of general formula (VII) and (IV) as has just been stated, and then to add the alkali metal salt of the acid of general formula (II) to the reaction mixture.

As will be realized by those skilled in the art, some radicals falling within the definition of the symbol R are incompatible with the reactants employed during the reactions, and must be protected prior to carrying out the processes, or some phases of the processes, described above. This is the case, in particular, when the radical R contains primary or secondary amino groups or hydroxyl groups which are capable of giving rise to side reactions. In this case, the said groups must be protected by any method known to those skilled in the art, and then unblocked after reaction.

The new products of general formula (I) may be purified by the usual known methods, e.g. by crystallization, chromatography or successive extractions in acidic and basic medium.

The new products of general formula (I) may be converted into addition salts with acids, by the action of an acid in an organic solvent such as an alcohol, a ketone, an ether or a chlorinated solvent. The salt formed precipitates, where appropriate after concentration of its solution; it is separated by filtration or decantation.

The products of general formula (I) possess especially advantageous pharmacological properties, which reveal an anxiolytic, hypnotic, anticonvulsant, antiepileptic and muscle relaxant activity. Thus, the show appreciable affinity in vitro for benzodiazepine receptor sites at concentrations between 0.4 and 200 nM according to the technique described by J. C. BLANCHARD and L. JULOU, J. of Neurochemistry, 40, 601 (1983) modelled on the work of SQUIRES and BRAESTRUP, Nature, 266, 732 (1977).

In animals (mice), they have been shown to be active, at doses which are generally between 0.3 and 200 mg/kg orally, with respect to pentetrazole-induced convulsions according to a technique close to that of EVERETT and RICHARDS, J. Pharmacol., 81, 402 (1944).

The new products of general formula (I) and their salts possess, in addition, low toxicity. Their oral LD₅₀ is generally between 300 and 900 mg/kg in mice.

For medicinal use, the new products of general formula (I) may be employed as they are or in the form of pharmaceutically acceptable salts, i.e. salts which are non-toxic at the doses at which they are used.

As examples of pharmaceutically acceptable salts, there may be mentioned the addition salts with inorganic acids, such as hydrochlorides, sulphates, nitrates and phosphates, or with organic acids, such as acetates, propionates, succinates, benzoates, fumarates, maleates, methanesulphonates, isethionates, theophyllineacetates, salicylates, phenolphthalinates and methylenebis(β-oxynaphthoates), or substitution derivatives of these compounds.

Of special value are the products of general formula (I) in which A forms with the pyrrole ring an isoindoline or 6,7-dihydro-5H-pyrrolo[3,4-b]pyrazine ring-system, Het denotes a 1,8-naphthyridin-2-yl radical substituted with a halogen atom or a (1 to 4 C) alkyloxy radical and R denotes a straight- or branched-chain alkyl radical of 1 to 6 carbon atoms which is unsubstituted or substituted by alkyloxy, dialkylamino, alkylcarbonylamino, 1-piperazinyl, piperidino, piperidinocarbonyl or phenyl, or R denotes 2-pyrrolidinyl or 3- or 4-piperidyl, the said alkyl radicals being straight- or branched-chain radicals and containing, except where specifically stated, 1 to 10 carbon atoms each, and the said piperazinyl, piperidino, piperidyl and pyrrolidinyl radicals being unsubstituted or substituted at any position by one or more alkyl or alkylcarbonyl radicals, or form a lactam group with the nitrogen atom of the ring.

The following products are of special value:
(RS)-2-(7-Chloro-1,8-naphthyridin-2-yl)-3-oxo-1-isoindolinyl 4-acetamidobutyrate and its (+) and (−) enantiomers.
(RS)-2-(7-Chloro-1,8-naphthyridin-2-yl)-3-oxo-1-isoindolinyl 1-propionyl-4-piperidinecarboxylate;
(RS)-2-(7-Methoxy-1,8-naphthyridin-2-yl)-3-oxo-1-isoindolinyl 5-methylhexanoate; and
(RS)-2-(7-Chloro-1,8-naphthyridin-2-yl)-3-oxo-1-isoindolinyl 3-diisopropylaminopropionate.

EXAMPLES

The Examples which follow show how the invention may be put into practice.

EXAMPLE 1

3-Dimethylaminopropionic acid hydrochloride 9.2 g) and 1,8-diazabicyclo[5.4.0]undec-7-ene (16.7 g) are added at a temperature in the region of 20° C. to a solution, maintained under an argon atmosphere, of 3-chloro-2-(7-chloro-1,8-naphthyridin-2-yl)-1-isoindolinone (16.5 g) in anhydrous dimethylformamide (100 cc), and the suspension obtained is stirred for 24 hours at a temperature in the region of 20° C. Distilled water (200 cc) and dichloromethane (200 cc) are then added. The aqueous phase is separated after settling has occurred and then re-extracted with dichloromethane (3×50 cc).

The organic phases are combined, washed with distilled water (2×50 cc), dried over magnesium sulphate, filtered and then concentrated to dryness under reduced pressure (2.7 kPa) at 80° C. The residue obtained is dissolved in dichloromethane (100 cc) and the solution extracted with 1N aqueous hydrochloric acid solution (2×100 cc). The aqueous phases are combined, washed with dichloromethane (50 cc), alkalinized with 10 N sodium hydroxide solution to a pH in the region of 11 and extracted with dichloromethane (2×150 cc). The organic phases are combined, washed with distilled water (2×30 cc), dried over magnesium sulphate, filtered and then concentrated to dryness under reduced pressure (2.7 kPa) at 60° C. After the product thereby obtained has been recrystallized twice successively in ethanol, 2-(7-chloro-1,8-naphthyridin-2-yl)-3-oxo-1-isoindolinyl 3-dimethylaminopropionate (2.9 g), m.p. 150° C., is obtained.

3-Dimethylaminopropionic acid hydrochloride may be obtained by the method described by CLARKE H. T., GILLESPIE H. B. and WEISSHAUS S. Z., J. Am. Chem. Soc., 55, 4571 (1933).

3-Chloro-2-(7-chloro-1,8-naphthyridin-2-yl)-1-isoindolinone may be prepared in the following manner: sulphinyl chloride (200 cc) is added dropwise with stirring to 3-hydroxy-2-(7-methoxy-1,8-naphthyridin-2-yl)-1-isoindolinone (15.5 g). The reaction mixture is heated to reflux with stirring for 1 hour, then treated with dimethylformamide (10.5 cc) and heated again to reflux for 3 hours, then cooled to a temperature in the region of 60° C. and concentrated to dryness under reduced pressure (2.7 kPa) at 60° C. Dichloromethane (100 cc) is added to the residue obtained, and the mixture is concentrated to dryness under reduced pressure (2.7 kPa) at 60° C. Dichloromethane 100 cc) is added to the residual solid obtained and the mixture is stirred for 10 minutes. The insoluble product is separated by filtration and washed with dichloromethane (15 cc) and then with diisopropyl ether (2×25 cc) and dried in the air. 3-Chloro-2-(7-chloro-1,8-naphthyridin-2-yl)-1-isoindolinone (12.4 g), which has not melted at 300° C., is thereby obtained. 3-Hydroxy-2-(7-chloro-1,8-naphthyridin-2-yl)-1-isoindolinone can be prepared by the method described in Belgian Patent No. 815019.

EXAMPLE 2

Working in a manner similar to that described in Example 1, but starting with 3-chloro-2-(7-chloro-1,8-naphthyridin-2-yl)-1-isoindolinone (8.25 g), 4-dimethylaminobutanoic acid hydrochloride (4.25 g) and 1,8-diazabicyclo[5.4.0]undec-7-ene (7.6 g), 2-(7-chloro-1,8-naphthyridin-2-yl)-3-oxo-1-isoindolinyl 4-dimethylaminobutanoate (4.1 g), m.p. 148° C., is obtained.

4-Dimethylaminobutanoic acid may be prepared by the method described by C. HARRIES and F. DUVEL, Liebigs Ann. Chem., (1915) 410, 54.

EXAMPLE 3

4-Methylpentanoic acid (2.4 g) and 1,8-diazabicyclo[5.4.0]undec-7-ene (3.05 g) are added at a temperature in the region of 20° C. to a solution, maintained under an argon atmosphere, of 3-chloro-2-(7-chloro-1,8-naphthyridin-2-yl)-1-isoindolinone (6.6 g) in anhydrous dimethylformamide (60 cc), and the suspension obtained is stirred for 24 hours at a temperature in the region of 20° C. Distilled water (500 cc) and dichloromethane (150 cc) are then added. The aqueous phase is separated after settling has occurred and then re-extracted with dichloromethane (2×150 cc). The organic phases are combined, washed with distilled water (3×50 cc), dried over magnesium sulphate, filtered and then concentrated to dryness under reduced pressure (2.7 kPa) at 60° C. The oily residue is purified by chromatography on silica gel (150 g) contained in a column 3.5 cm in diameter [eluant: dichloromethane/methanol (98.2 by volume)]. Elution is first performed with 200 cc of solvent: the corresponding eluate is discarded; elution is then performed with 900 cc of solvent: the corresponding eluate is concentrated to dryness under reduced pressure (2.7 kPa) at 40° C. After recrystallization in ethanol, 2-(7-chloro-1,8-naphthyridin-2-yl)-3-oxo-1-isoindolinyl 4-methylpentanoate (4 g), m.p. 147° C., is obtained.

EXAMPLE 4

Working as in Example 1, but starting with 3-chloro-2-(7-chloro-1,8-naphthyridin-2-yl)-1-isoindolinone (9.9 g) in anhydrous dimethylformamide (100 cc), 1-methyl-3-piperidinecarboxylic acid hydrochloride (5.4 g) and 1,8-diazabicyclo[5.4.0]undec-7-ene (10.7 g), a product (11.3 g), m.p. about 70° C., is obtained after precipitation in water (1000 cc), filtration and drying in the air. The solid obtained is dissolved in ethanol (40 cc). A solution of fumaric acid (3 g) in ethanol (30 cc) is added to the hot solution obtained. The crystallized product obtained is separated by filtration, washed with ethanol (15 cc) and dried under reduced pressure (0.07 kPa) at 45° C. 2-(7-Chloro-1,8-naphthyridin-2-yl)-1-oxo-3-isoindolinyl 1-methyl-3-piperidinecarboxylate acid fumarate (9.8 g), m.p. 211° C., is thereby obtained.

1-Methyl-3-piperidinecarboxylic acid hydrochloride may be prepared in the following manner: ethyl 1-methyl-3-piperidinecarboxylate (17.1 g) is dissolved in 6N aqueous hydrochloric acid solution (67 cc). After 6 hours under reflux, the solution is concentrated to dryness and the residue recrystallized in acetone. 1-Methyl-3-piperidinecarboxylic acid hydrochloride (15.7 g), m.p. 186° C., is thereby obtained.

EXAMPLE 5

Working as in Example 1, but starting with 3-chloro-2-(7-chloro-1,8-naphthyridin-2-yl)-1-isoindolinone (9.9 g) in anhydrous dimethylformamide (100 cc), 1methyl-4-piperidinecarboxylic acid hydrochloride (5.4 g) and 1,8-diazabicyclo[5.4.0]undec-7-ene (10.7g), and after the residue obtained has been recrystallized twice successively in ethanol and then in acetonitrile, 2-(7-chloro-1,8-naphthyridin-2-yl)-1-oxo-3-isoindolinyl 1-methyl-4-piperidinecarboxylate (5.6 g), m.p. 136° C. and then 157° C., is obtained.

1-Methyl-4-piperidinecarboxylic acid hydrochloride may be prepared according to the method described in Example 4 for the preparation of 1-methyl-3-piperidinecarboxylic acid hydrochloride, but starting with ethyl 1-methyl-4-piperidinecarboxylate (8.6 g) and 6N aqueous hydrochloric acid solution (33 cc). After recrystallization in acetone, 1-methyl-4-piperidinecarboxylic acid hydrochloride (6.5 g), m.p. 231° C., is obtained.

Ethyl 1-methyl-4-piperidinecarboxylate may be prepared in the following manner: to a solution, maintained at a temperature in the region of 5° C., of ethyl 4-piperidinecarboxylate (15.7 g) in water (8 cc), a 37% strength (weight/volume) solution (20.3 cc) of formaldehyde is added in the course of 15 minutes at the same temperature, followed, again in the course of 15 minutes, by formic acid (11.5 g). The mixture is heated for 4 hours under reflux, then cooled, and brought to a pH in the region of 10 using 10N aqueous sodium hydroxide solution. After extraction with methylene chloride (3×150 cc), washing the organic extracts with water, drying and concentration to dryness under reduced pressure (2.7 kPa) at 70° C., ethyl 1-methyl-4-piperidinecarboxylate (13.5 g) is obtained in the form of an oil, which is employed in the crude state in the subsequent syntheses.

EXAMPLE 6

Working as in Example 1, but starting with 3-chloro-2-(7-chloro-1,8-naphthyridin-2-yl)-1-isoindolinone (6.9 g) in anhydrous dimethylformamide (70 cc), 3-diisopropylaminopropionic acid hydrochloride (4.4 g) and 1,8-diazabicyclo-[5.4.0]undec-7-ene (7.45 g), and after the residue obtained has been recrystallized successively, first in acetonitrile and then in ethanol, 2-(7-chloro-1,8-naphthyridin-2-yl)-3-oxo-1-isoindolinyl 3-diisopropylaminopropionate (2.7 g), m.p. 135° C., is obtained.

3-Diisopropylaminopropionic acid hydrochloride may be obtained by working according to the method described in Example 4 for the preparation of 1-methyl-3-piperidinecarboxylic acid, but starting with ethyl 3-diisopropylaminopropionate (5 g) and 6N aqueous hydrochloric acid solution (35 cc). After the product obtained has been recrystallized in acetone, 3-diisopropylaminopropionic acid hydrochloride (2.3 g), m.p. 170° C., is obtained.

Ethyl 3-diisopropylaminopropionate may be obtained in the following manner: ethyl 3-bromopropionate (18.1 g) is introduced dropwise in the course of 30 minutes into a solution of diisopropylamine (28.5 cc) and ethanol (40 cc) maintained at a temperature of 25° C. The suspension obtained is heated to reflux for 4 hours. After being cooled, the reaction mixture is taken up with water (100 cc) and 4N aqueous hydrochloric acid solution (70 cc). After the mixture is washed with ethyl ether (100 cc), it is alkalinized to a pH in the region of 9 with 4N aqueous sodium hydroxide solution. The oil formed is extracted with methylene chloride (3×150 cc). After being washed with water (2×100 cc) and dried, the methylene chloride solution obtained is concentrated to dryness under reduced pressure (2.7 kPa) at 40° C. Ethyl 3-diisopropylaminopropionate (11.6 g) is thereby obtained in the form of an oil, which is employed in the crude state in the subsequent syntheses.

EXAMPLE 7

Triethylamine (27 cc) is added to a solution, maintained at a temperature in the region of 20° C., of 2-(7-methoxy-1,8-naphthyridin-2-yl)-3-hydroxy-1-isoindolinone (12.3 g) in methylene chloride (200 cc). 4-Methylpentanoyl chloride (10.8 g) and 4-dimethylaminopyridine (50 mg) are then introduced dropwise in the course of 20 minutes, and the reaction mixture is then heated for 19 hours under reflux. The suspension obtained is poured into water (800 cc) and the solid obtained is separated by filtration and removed. The organic phase is separated after settling has occurred, washed with water, dried and concentrated to dryness under reduced pressure (2.7 kPa). The oily residue obtained is purified by chromatography on silica gel (0.063–0.2 mm; 150 g) contained in a column 2.7 cm in diameter (eluant: methylene chloride), eluting 50-cc fractions. Fractions 6 to 18 are combined and concentrated to dryness under reduced pressure (2.7 kPa) at 40° C. After the solid obtained has been recrystallized in acetonitrile, 2-(7-methoxy-1,8-naphthyridin-2-yl)-3-oxo-1-isoindolinyl 4-methylpentanoate (4.9 g), m.p. 133° C., is obtained.

4-Methylpentanoyl chloride may be prepared according to F. Kogl and C. A. Salemink, Rec. Trav. Chim. 71, 779–97 (1952).

EXAMPLE 8

Working as in Example 1, but starting with 3-chloro-2-(7-chloro-1,8-naphthyridin-2-yl)-1-isoindolinone (9.9 g) in anhydrous dimethylformamide (100 cc), 1-acetyl-4-piperidinecarboxylic acid (5.1 g) and 1,8-diazabicyclo-[5.4.0]-undec-7-ene (4.6 g), and after successive recrystallization in a mixture of acetone and water (2:1 by volume) and then in ethanol, 2-(7-chloro-1,8-naphthyridin-2-yl)-3-oxo-1-isoindolinyl 1-acetyl-4-piperidinecarboxylate (7.5 g), m.p. 101° C., is obtained.

EXAMPLE 9

Working as in Example 1, but starting with 3-chloro-2-(7-chloro-1,8-naphthyridin-2yl)-1-isoindolinone (9.9 g) in anhydrous dimethylformamide (100 cc), 5-methylhexanoic acid (3.9 g) and 1,8-diazabicyclo[5.4.0]undec-7-ene (4.6 g), and after recrystallization in ethanol, 2-(7-chloro-1,8-naphthyridin-2-yl)-3-oxo-1-isoindolinyl 5-methylhexanoate (8 g), m.p. 132° C., is obtained.

EXAMPLE 10

The procedure is as in Example 7, but starting with 2-(7-methoxy-1,8-naphthyridin-2-yl)-3-hydroxy-1-isoindolinone (6.8 g) in methylene chloride (100 cc), triethylamine (10.1 g), 5-methylhexanoyl chloride (6.4 g) and 4-dimethylaminopyridine (50 mg). The residue obtained after treatment is purified by chromatography on silica gel (0.063–0.2 mm; 100 g) contained in a column 2.8 cm in diameter (eluant: methylene chloride), collecting 30-cc fractions. Fractions 19 to 94 are combined and concentrated to dryness under reduced pressure (2.7 kPa). After the residue obtained has been recrystallized in heptane (75 cc), 2-(7-methoxy-1,8-naphthyridin-2-yl)-3-oxo-1-isoindolinyl 5-methylhexanoate (5.6 g), m.p. 105° C., is obtained.

EXAMPLE 11

Working as in Example 1, but starting with 3-chloro-2-(7-chloro-1,8-naphthyridin-2-yl)-1-isoindolinone (9.9 g) in anhydrous dimethylformamide (100 cc), 1-propionyl-4-piperidinecarboxylic acid (5.5 g) and 1,8-diazabicyclo[5.4.0]undec-7-ene (4.6 g), and by recrystallization in ethanol, 2-(7-chloro-1,8-naphthyridin-2-yl)-3-oxo-1-isoindolinyl 1-propionyl-4-piperidinecarboxylate (4.9 g), m.p. 189° C., is obtained.

1-Propionyl-4-piperidinecarboxylic acid may be prepared in the following manner: a mixture of 4-piperidinecarboxylic acid (25.8 g) and propionic anhydride (100 cc) is heated for 2 hours 30 minutes to a temperature in the region of 135° C. The reaction mixture is concentrated to dryness under reduced pressure (2.7 kPa) and the oily residue is taken up with methylene chloride (200 cc). The methylene chloride solution obtained is washed with water (4×80 cc), dried and concentrated to dryness under reduced pressure (2.7 kPa). The oil obtained is crystallized by stirring with ethyl ether (50 cc). 1-Propionyl-4-piperidinecarboxylic acid (5.8 g), m.p. 91°–94° C., is thereby obtained.

EXAMPLE 12

Working as in Example 1, but starting with 3-chloro-2-(7-chloro-1,8-naphthyridin-2-yl)-1-isoindolinone (29.7 g) in anhydrous dimethylformamide (300 cc), 4-acetamidobutyric acid (13.1 g) and 1,8-diazabicyclo[5.4.0]-undec-7-ene (13.7 g), 2-(7-chloro-1,8-naphthyridin-2yl)-3-oxo-1-isoindolinyl 4-acetamidobutyrate (18 g), m.p. 186° C., is obtained after recrystallization in acetonitrile.

EXAMPLE 13

The procedure is as in Example 1, but starting with 3-chloro-2-(7-chloro-1,8-naphthyridin-2-yl)-1-isoindolinone (4.95 g) in anhydrous dimethylformamide (60 cc), phenylacetic acid (2.05 g) and 1,8-diazabicyclo[5.4.0]-undec-7-ene (2.25 g). After recrystallization in ethyl acetate, 2-(7-chloro-1,8-naphthyridin-2-yl)-3-oxo-1-isoindolinyl phenylacetate (4.4 g), m.p. 222°–224° C., is obtained.

EXAMPLE 14

The procedure is as in Example 1, but starting with 3-chloro-2-(7-chloro-1,8-naphthyridin-2-yl)-1-isoindolinone (9.9 g) in anhydrous dimethylformamide (100 cc), DL-pyroglutamic acid (3.9 g) and 1,8-diazabicyclo[5.4.0]-undec-7ene (4.6 g). After recrystallization in dimethylformamide, 2-(7-chloro-1,8-naphthyridin-2-yl)-3-oxo-1-isoindolinyl 5-oxo-2-pyrrolidinecarboxylate (8.8 g), m.p. 255° C. (decomposition), is obtained.

EXAMPLE 15

The procedure is as in Example 1, but starting with 3-chloro-2-(7-chloro-1,8-naphthyridin-2-yl)-1-isoindolinone (9.9 g) in anhydrous dimethylformamide (100 cc), N,N-pentamethylenesuccinamic acid (5.55 g) and 1,8-diazabicyclo[5.4.0]undec-7-ene (4.6 g). After recrystallization successively in acetonitrile and then in ethanol, 2-(7-chloro-1,8-naphthyridin-2-yl)-3-oxo-1-isoindolinyl N,N-pentamethylenesuccinamate (7.5 g), m.p. 199° C., is obtained.

N,N-Pentamethylenesuccinamic acid may be prepared according to D. Pressman, J. M. Bryden and L. Pauling, J. Am. Chem. Soc., 70, 1352 (1948).

EXAMPLE 16

Working as in example 1, but starting with 3-chloro-2-(7-chloro-1,8-naphthyridin-2-yl)-1-isoindolinone (9.9 g) in anhydrous dimethylformamide (100 cc), 3-(2,6-dimethylpiperidino)propionic acid hydrochloride (6.7 g) and 1,8-diazabicyclo[5.4.0]undec-7-ene (10.7 g), 2-(7-chloro-1,8-naphthyridin-2-yl)-3-oxo-1-isoindolinyl 3-(2,6-dimethylpiperidino)propionate (6 g), m.p. 159° C., is obtained after recrystallization in ethanol.

3-(2,6-Dimethylpiperdino)propionic acid hydrochloride may be obtained by working according to the method described in Example 4 for the preparation of 1-methyl-3-piperidinecarboxylic acid hydrochloride, but starting with ethyl 3-(2,6-dimethylpiperidino)propionate hydrochloride (12.5 g) and 6N aqueous hydrochloric acid solution (35 cc). 3-(2,6-Dimethylpiperidino)propionic acid hydrochloride, m.p. 215° C., is thereby obtained.

Ethyl 3-(2,6-dimethylpiperidino)propionate hydrochloride may be obtained by working according to the method described in Example 6 for the preparation of ethyl 3- diisopropylaminopropionate, but starting with ethyl 3bromopropionate (18.1 g), 2,6-dimethylpiperidine (27 cc) and ethanol (30 cc). The reaction mixture is concentrated to dryness under reduced pressure (2.7 kPa) and the residue obtained is taken up with water (50 cc) and 4N aqueous hydrochloric acid solution (30 cc). The aqueous phase is washed with ethyl ether (2×80 cc) and neutralized with 4N aqueous sodium hydroxide solution (40 cc). The insoluble oil is extracted with ethyl ether (3×120 cc); the organic extracts are then washed with water (2×80 cc) and concentrated to dryness under reduced pressure (2.7 kPa) at 40° C. The residue is dissolved in ethyl ether (100 cc). A 4.5N solution (13.4 cc) of gaseous hydrochloric acid in ethyl ether is added to the solution obtained. A product precipitates. It is separated by filtration, washed and dried in the air. Ethyl 3-(2,6-dimetylpiperidino)-propionate hydrochloride (14.4 g), m.p. 146° C., is thereby obtained.

Example 17

Working as in Example 1, but starting with 3- chloro-2-(7-chloro-1,8-naphthyridin-2-yl)-1- isoindolinone (9.9 g) in anhydrous dimethylformamide (100 cc), 4-piperidinobutyric acid hydrochloride (6.2 g) and 1,8-di-azabicyclo[5.4.0]-undec-7-ene (10.7 g), 2-(7-chloro-1,8- naphthyridin-2-yl)-3-oxo-1- isoindolinyl 4-piperdino butyrate (9.4 g), m.p. 166° C., is obtained after recrystallization in ethanol.

4-Piperidinobutyric acid hydrochloride may be obtained by working according to the method described in Example 4 for the preparation of 1-methyl-3-piperidinecarboxylic acid hydrochloride, but starting with ethyl 4-piperidinobutyrate (19.9 g) and 6N aqueous hydrochloric acid solution (66.5 cc), and by heating for 24 hours under reflux. 4-Piperidinobutyric acid hydrochloride (16.3 g), m.p. 190° C., is thereby obtained.

Ethyl 4-piperdinobutyrate may be prepared by working according to the method described in Example 6 for the preparation of ethyl 3-diisopropylaminopropionate, but starting with ethyl 4-bromobutyrate (48.8 g), piperidine (42.5 g) and ethanol (75 cc). The reaction mixture is taken up with water (200 cc) and 4N aqueous hydrochloric acid solution (120 cc). After being washed with ethyl ether (150 cc, the aqueous phase is alkalinized to a pH in the region of 9 with 4N aqueous sodium hydroxide solution. The oil formed is extracted with methylene chloride (3×150 cc). The organic extracts are combined, washed with water, dried and concentrated to dryness under reduced pressure (2.7 kPa) at 70° C. Ethyl 4-piperidinobutyrate (47 g) is thereby obtained in the form of an oil, which is employed in the crude state in the subsequent syntheses.

Example 18

The procedure is as in Example 1, but starting with 3-chloro-2-(7-chloro-1,8-naphthyridin-2-yl)-1-isoindolinone (4,3 g) in anhydrous dimethylformamide (40 cc), 3-(2-oxopiperidino)propionic acid (2.2 g) and 1,8-diazabicyclo [5.4.0]undec-7-ene (2 g). After the reaction mixture has been taken up with water, the resulting mixture extracted with methylene chloride and the solvent evaporated, the residue obtained is recrystalized in acetonitrile. The product thereby obtained is purified by chromatography on silica (0.063–0.2 mm; 100 g) contained in a column 2.3 cm in diameter (eluant: methylene chloride), collecting 50-cc fractions. Fractions 56 to 64 are combined and concentrated to dryness under reduced pressure (2.7 kPa) at 20° C. The residue obtained is recrystallized in acetonitrile. 2-(7-Chloro-1,8-naphthridin-2-yl)-3-oxo-1-isoindolinyl 3-(2- oxopiperidino)propionate (2.8 g), m.p. 175° C., is thereby obtained.

3-(2-Oxopiperidino)propionic acid may be prepared in the following manner: a solution of potassium hydroxide (3.8 g) in water (15 cc) is added to a solution of methyl (3-(2-oxopiperidino)propionate (9.2 g) in ethanol (40 cc). The reaction mixture is stirred for 20 hours at a temperature in the region of 20° C. and then evaporated to dryness under reduced pressure (2.7 kPa). The residue is taken up with water (100 cc). The solution obtained is washed with ethyl ether (50 cc), then acidified to a pH in the region of 1 with 4N aqueous hydrochloric acid solution and extracted with methylene chloride (3×100 cc). After being washed with water and dried, the methylene chloride solution is concentrated to dryness under reduced pressure (2.7 kPa). 3-(2-Oxopiperidino)propionic acid (2.3 g), m.p. 105°–110° C., is thereby obtained.

Methyl 3-(2-oxopiperidino)propionate may be prepared according to the method described by H. TAKAHATA et al., Chem. Pharm. Bull., 28 (12), 3632-8 (1980).

Example 19

Working in a manner similar to that described in Example 1, but starting with 5-chloro-6-(7-chloro-1,8-naphthyridin-2-yl)-7-oxo-6,7-dihydro-5H-pyrrolo-[3,4-b]-pyrazine (9.9 g), 1,8-diazabicyclo[5.4.0]undec-7-ene (9.6 g) and 3-dimethylaminopropionic acid hydrochloride (4.8 g), 6-(7-chloro-1,8-naphthyridin-2-yl)-7-oxo-6,7-dihydro-5H-pyrrolo[3,4-b]pyrazin-5-yl 3-dimethylaminopropionate (2.2 g), m.p. 200° C., is obtained after recrystallization in acetonitrile.

5-Chloro-6-(7-chloro-1,8-naphthyridin-2-yl)-7-oxo-6,7-dihydro-5H-pyrrolo[3,4-b]pyrazine may be prepared in the following manner: sulphinyl chloride (300 cc) is added dropwise with stirring to 5-hydroxy-6-(7-methoxy-1,8-naphthyridin2-yl)-7-oxo-6,7-dihydro-5H-pyrrolo[3,4-b]-pyrazine (23.2 g). The reaction mixture is heated to reflux with stirring for 1 hour, then treated with dimethylforamide (1 cc) and heated again to reflux for 3 hours, then cooled to a temperature in the region of 60° C. and concentrated to dryness under reduced pressure (2.7 kPa). Dichloromethane (100 cc) is added to the residue obtained and the mixture is concentrated to dryness under reduced pressure (2.7 kPa). Dichloromethane (100 cc) is added to the residual solid obtained and the mixture stirred for 10 minutes. The insoluble product is separated by filtration and washed with dichloromethane (15 cc) and then with diisopropyl ether (2×25 cc), and dried in the air. 5-Chloro-6-(7-chloro-1,8-naphthyridin-2-yl)-7-oxo-6,7-dihydro-5H-pyrrolo[3,4b]pyrazine (21 g), m.p. 264° C., is thereby obtained.

5-Hydroxy-6-(7-methoxy-1,8-naphthyridin-2-yl)-7-oxo-6,7-dihydro-5H-pyrrolo[3,4-b]pyrazine may be prepared by the method described in Belgian Patent No. 815,019.

3-Dimethylaminopropionic acid dihydrochloride may be prepared by the method of CLARKE H. T. et al., J. Am. Chem. Soc., 55, 4571 (1933).

Example 20

Sodium (4-acetyl-1-piperazinyl)acetate (4.2 g) is added to a solution, maintained at a temperature in the region of 20° C., of 3-chloro-2-(7-chloro-1,8-naphthyridin-2yl)-1-isoindolinone (6.6 g) in anhydrous dimethylformamide (60 cc), and the reaction mixture is maintained for 15 hours at a temperature in the region of 20° C. 1,8-Diazabicyclo[5.4.0]undec-7-ene (3g) is then added, and the mixture is then stirred again for 24 hours at a temperature in the region of 20° C. The reaction mixture is taken up with water (250 cc) and extracted with methylene chloride (3×150 cc). After the organic phase has been washed with water and concentrated to dryness under reduced pressure (2.7 kPa), the residue obtained is recrystallized in ethanol. 2-(7-Chloro-1,8-naphthyridin-2-yl-)-3-oxo-1-isoindolinyl (4-acetyl-1-piperazinyl)acetate (3.7 g), m.p. 192° C., is thereby obtained.

Sodium (4-acetyl-1-piperazinyl)acetate may be prepared in the following manner: ethyl (4-acetyl-1-piperazinyl)acetate (4.3 g) is added to a mixture of ethanol (20 cc) and 1N aqueous sodium hydroxide solution (20 cc). The reaction mixture is stirred for 20 hours at a temperature in the region of 20° C. and is then concentrated to dryness under reduced pressure (2.7 kPa) at 80° C. The solid obtained is suspended in isopropyl ether (80 cc) and stirred, then separated by filtration and dried. Sodium (4-acetyl-1-piperazinyl)acetate (4.3 g), which melts between 100° and 105° C., is thereby obtained.

Ethyl (4-acetyl-1-piperazinyl)acetate may be prepared according to the method described by D. NARDI and E. MASSARANI, J. Med. Chem. 14, 635 (1971).

Example 21

Working as in Example 1, but starting with 3-chloro-2-(7-chloro-1,8-naphthyridin-2-yl)-1-isoindolinone (9.9 g) in anhydrous dimethylformamide (100 cc), 4propionamidobutanoic acid (4.8 g) and 1,8-diazabicyclo[5.4.0]-undec-7-ene (4.6 g), 2-(7-chloro-1,8-napthyridin-2-yl)-3-oxo-1-isoindolinyl 4-propionamidobutyrate(6.6 g), m.p. 179° C., is obtained after recrystallization in acetonitrile.

4-Propionamidobutanoic acid may be prepared in the following manner: 4-aminobutyric acid (10.3 g) is added in the course of 15 minutes to propionic anhydride (10 cc) at a temperature in the region of 20° C., followed by 5 drops of concentrated sulphuric acid (d=1.83), and the mixture is heated to a temperature in the region of 100° C. for 2 hours. After the mixture is cooled, the crystallized solid is separated by filtration, washed with ethyl ether (5×100 cc) and dried. 4-Propionamidobutanoic acid (9.8 g), m.p. 85°–90° C., is thereby obtained.

Example 22

To a solution, maintained at a temperature in the region of 20° C., of 2-(7-methoxy-1,8-naphthyridin-2-yl)-3-hydroxy-1-isoindolinone (9.2 g) and triethylamine (20 cc) in 1,2-dichloroethane (150 cc), there is added, in the course of 20 minutes, a solution of 2-methylpropoxyacetyl chloride (9 g) in 1,2-dichloroethane (20 cc) followed by 4-dimethylaminopyridine (50 mg), and the mixture is heated to reflux for 16 hours. The reaction mixture is poured into water (250 cc) and then extracted with methylene chloride (100 cc.) After the extract is washed with water, dried and concentrated to dryness under reduced pressure (3kPa), the residue obtained is purified by two successive recrystallizations in ethanol. 2-(7-Methoxy-1,8-naphthyridin-2-yl)-3-oxo-1-isoindolinyl 2-methylpropoxyacetate (7.9 g), m.p. 114° C., is thereby obtained.

2-Methylpropoxyacetyl chloride may be obtained in the following manner: thionyl chloride (5 cc) is added in the course of 15 minutes to a solution of 2-methylpropoxyacetic acid (8.3 g) in chloroform (50 cc). The mixture is heated for 5 hours under reflux and then evaporated to dryness under reduced pressure (2.7 kPa). 2-Methylpropoxyacetyl chloride (7.5 g) is thereby obtained in the form of an oil, which is employed in the crude state in the subsequent syntheses.

2-Methylpropoxyacetic acid may be obtained in the following manner: sodium (12.7 g) is added to isobutyl alcohol (200 cc) maintained at a temperature in the region of 100° C., and the mixture is heated until the sodium has disappeared. Chloroacetic acid (23.6 g) is then added in the course of 1 hour, and heating is continued for 2 hours. After being cooled, the reaction mixture is poured into water (250 cc). The aqueous phase is washed with ethyl ether (200 cc), concentrated to half the volume under reduced pressure (3 kPa) and then acidified to a pH in the region of 1 with 1N aqueous hydrochloric acid solution. The oil formed is extracted with ethyl ether (3×150 cc). The organic phase is washed with water, dried and concentrated in dryness under reduced pressure (3 kPa). After the residue obtained has been distilled under reduced pressure, 2-methylpropoxyacetic acid (21.8 g), b.p. 92°–96° C. (0.93 kPa), is obtained.

Example 23

The procedure is as in Example 1, but starting with 3-chloro-2-(7-chloro-1,8-naphthyridin-2-yl)-1-isoindolinone (6.6 g) in anhydrous dimethylformamide (60 cc), 1-isopropyl-4-piperidinecarboxylic acid hydrochloride (4.3 g) and 1,8-diazabicyclo[5.4.0]undec-7-ene (7.1 g). After recrystallization in acetonitrile, a solid (4.1 g) is obtained, which is dissolved in ethanol (120 cc) under reflux; fumaric acid (1.03 g) dissolved in ethanol (20 cc) is added. After crystallization in acetonitrile, 2-(7-chloro-1,8-naphthyridin-2-yl)-3-oxo-1-isoindolinyl 1-isopropyl-4-piperidinecarboxylate acid fumarate (4.9 g), m.p. 184° C., is obtained.

1-Isopropyl-4-piperdinecarboxylic acid hydrochloride may be prepared according to the method described in Example 4 for the preparation of 1-methyl-3-piperidinecarboxylic acid hydrochloride, but starting with ethyl 1-isopropyl-4-piperidinecarboxylate hydrochloride (65.5 g) and 6N aqueous hydrochloric acid solution (18.6 cc). 1-Isopropyl-4 -piperidinecarboxylic acid hydrochloride (4.5 g), m.p. 260–265° C., is thereby obtained.

Ethyl 1-isopropyl-4-piperidinecarboxylate hydrochloride may be prepared in the following manner: ethyl 4-piperdinecarboxylate (15.7 g) is added in the course of 10 minutes at a temperature in the region of 25° C. to a solution of 2-bromopropane (6.15 g) in propanol (50 cc). The reaction mixture is heated for 48 hours under reflux and then concentrated to dryness under reduced pressure (2.7 kPa). The residue is taken up with 1.5N aqueous hydrochloric acid solution (1.50 cc) and the solution obtained is washed with ethyl ether (2×100 cc). The aqueous phase is alkalinized to a pH in the region of 9 with 4N aqueous sodium hydroxide solution, and extracted with methylene chloride (3×100 cc). The organic phase is washed with water, dried and concentrated to dryness under reduced pressure (2.7 kPa) at 40° C. The residue obtained is dissolved in ethanol (30 cc). A 4.5N solution (12 cc) of gaseous hydrochloric acid in ethyl ether is added to the solution obtained. The precipitate formed is separated by filtration, washed and dried. Ethyl 1-isopropyl-4-piperidinecarboxylate hydrochloride (6.9 g), m.p. 195°–200° C., is thereby obtained.

Example 24

3-Chloro-2-(7-chloro-1,8-naphthyridin-2-yl)-1- isoindolinone (6.6 g) is added to a solution of N-acetyl-β-alanine (3.9 g) in dimethylformamide (66 cc). 1,8-Diazabicyclo[5.4.0]undec-7-ene (3.8 g) is added dropwise to the beige suspension obtained, and the mixture is stirred at a temperature in the region of 20° C. for 18 hours. N-acetyl-β-alanine )1 g) is added again, followed by 1,8-diabicyclo[5.4.0]undec-7-ene (1 g), and the mixture is stirred at a temperature in the region of 20° C. for 24 hours. The reaction mixture is then poured into water (130 cc). The solid obtained is separated by filtration, washed with water (3×25 cc) and purified by chromatography under pressure (50 kPa) on silica (500 g) contained in a column 5 cm in diameter [eluant: dichloromethane/methanol (95:5 by volume)], collecting 75-cc fractions. Fractions 7 to 9 are combined and concentrated to dryness under reduced pressure (2.7 kPa). After the solid obtained has been recrystallized in acetonitrile, 2-(7-chloro-1,8-naphthyridin-2-yl)-3-oxo-1-isoindollinyl 3-acetamidopropanoate (3.9 g), m.p. 220° C., is obtained.

N-Acetyl-β-alanine may be prepared according to the method described in Example 21 for the preparation of 4-propionamidobutanoic acid, but starting with β-alanine (8.9 g) and acetic anhydride (9.6 g). N-Acetyl-β-alanine (12.9 g) is thereby obtained in the form of an oil, which is employed in the crude state in the subsequent syntheses.

EXAMPLE 25

The procedure is as in Example 24, but starting with 5-acetamidopentanoic acid (5 g) in dimethylformamide (66 cc), 3-chloro-2-(7-chloro-1,8-naphthyridin-2-yl)-1-isoindolinone (6.6 g) and 1,8-diazabicyclo[5.4.0]undec-7-ene (4.7 cc). After recrystallization in acetonitrile, 2-(7-chloro-1,8-naphthyridin-2-yl)-3-oxo-1-isoindolinyl 5-acetamidopentanoate (3.3 g), m.p. 185° C., is obtained.

5-Acetamidopentanoic acid may be prepared according to the method described in Example 21 for the preparation of 4-propionamidobutanoic acid, but starting with 5-aminopentanoic acid (11.7 g) and acetic anhydride (12.6 g). The reaction mixture is concentrated to dryness under reduced pressure (0.05 kPa) and 5-acetamidopentanoic acid (6 g) is thereby obtained in the form of an oil, which is employed in the crude state in the subsequent synthesis.

EXAMPLE 26

The procedure is as in Example 1, but starting with 3-chloro-2-(7-chloro-1,8-naphthyridin-2-yl)-1-isoindolinone (9.9 g) in anhydrous dimethylformamide (100 cc), 4-isobutyrylaminobutyric acid (5.2 g) and 1,8-diazabicyclo[5.4.0]undec-7-ene (4.6 g). The residue obtained is recrystallized in acetonitrile and then purified by chromatography on silica (0.063–0.2 mm; 130 g) contained in a column 3 cm in diameter [eluant: methylene chloride/methanol (98:2 by volume) mixture] collecting 25-cc fractions. Fractions 79 to 85 are combined and concentrated to dryness under reduced pressure (2.7 kPa). The residue obtained is crystallized by stirring in isopropyl ether. 2-(7-chloro-1,8-naphthyridin-2-yl)-3-oxo-1-isoindolinyl 4-isobutyrylaminobutyrate (5.5 g), m.p. 208° C., is thereby obtained.

4-Isobutyrylaminobutyric acid may be prepared according to the method described in Example 21 for the preparation of 4-propionamidobutanoic acid, but starting with 4-aminobutyric acid (10.3 g) and isobutyric anhydride (15.8 g). 4-Isobutyrylaminobutyric acid (15.5 g) is thereby obtained in the form of an oil, which is employed in the crude state in the subsequent syntheses.

EXAMPLE 27

The procedure is as in Example 1, but starting with 3-chloro-2-(7-chloro-1,8-naphthyridin-2-yl)-1-isoindolinone (9.9 g) in anhydrous dimethylformamide (100 cc), 1-butyryl-4-piperidinecarboxylic acid (6 g) and 1,8-diazabicyclo[5.4.0]undec-7-ene (4.6 g). The residue obtained is purified by chromatography on silica (0.063–0.2 mm; 250 g) contained in a column 4.2 cm in diameter [eluant: a mixture of methylene chloride and methanol (99:1 by volume)], collecting 70-cc fractions. Fractions 82 to 110 are combined and concentrated to dryness under reduced pressure (b 2.7 kPa). The solid obtained is taken up with stirring with isopropyl ether, then separated by filtration and dried. 2-(7-Chloro-1,8-naphthyridin-2-yl)-3-oxo-1-isoindolinyl 1-butyryl-4-piperidinecarboxylate (6 g), m.p. 165° C., is thereby obtained.

1-Butyryl-4-piperidinecarboxylic acid may be prepared according to the method described in Example 21 for the preparation of 4-propionamidobutanoic acid, but starting with 4-piperidinecarboxylic acid (12.9 g) and butyric anhydride (15.8 g). 1-Butyryl-4-piperidinecarboxylic acid (16 g), is thereby obtained in the form of an oil, which is employed in the crude state in the subsequent syntheses.

EXAMPLE 28

1,8-Diazabicyclo[5.4.0]undec-7-ene (10.7 g) is added dropwise to a suspension of 3-chloro-2-(7-chloro-1,8-naphthyridin-2-yl)-1-isoindolinone (9.9 g) and 4-diisopropylaminobutyric acid hydrochloride (6.7 g) in dimethylformamide (100 cc), and the mixture is stirred at a temperature in the region of 20° C. for 20 hours. The reaction mixture is then poured into water (130 cc). The solid obtained is separated by filtration and then dissolved in methylene chloride (200 cc). The organic extracts are washed with 0.1 N aqueous hydrochloric acid solution (2×35 cc), 0.5 N aqueous hydrochloric acid solution (35 cc), and then with water (2×35 cc). The organic phase is dried over magnesium sulphate, filtered and concentrated to dryness under reduced pressure (2.7 kPa). The residue obtained is taken up with methylene chloride (200 cc). The organic phase is washed with saturated aqueous sodium hydrogen carbonate solution (2×50 cc). The organic phase is dried over magnesium sulphate, filtered and concentrated to dryness under reduced pressure (2.7 kPa). The residue is recrystallized in isopropyl ether. 2-(7-Chloro-1,8-naphthyridin-2-yl)-3-oxo-1-isoindolinyl 4-diisopropylaminobutyrate (7.1 g), m.p. 118° C., is thereby obtained.

4-Diisopropylaminobutyric acid hydrochloride may be obtained by working according to the method described in Example 4 for the preparation of 1-methyl-3-piperidinecarboxylic acid hydrochloride, but starting with ethyl 4-diisopropylaminobutyrate (9.2 g) and 6 N aqueous hydrochloric acid solution (28.5 cc) and by heating for 6 hours under reflux. 4-Diisopropylaminobutyric acid hydrochloride (8 g), m.p. 136° C., is thereby obtained.

Ethyl 4-diisopropylaminobutyrate may be obtained in the following manner: diisopropylamine (40.4 g) is added dropwise to a solution of ethyl 4-bromobutyrate (39 g) in ethanol (80 cc). The solution obtained is heated to reflux for 6 hours. After the insoluble material formed has been filtered off, the filtrate is concentrated to dryness under reduced pressure (2.7 kPa). The residue is taken up with distilled water (15 cc) and 4 N aqueous hydrochloric acid solution (100 cc). The aqueous phase is washed with ethyl ether (3×75 cc) and then alkalinized with 10 N aqueous sodium hydroxide solution. The oil formed is extracted with ethyl ether (3×75 cc). The organic phase obtained is concentrated to dryness under reduced pressure (2.7 kPa). Ethyl 4-diisopropylaminobutyrate (9.2 g) is thereby obtained in the form of an oil, which is employed in the crude state in the subsequent syntheses.

EXAMPLE 29

Triethylamine (12.2 g), pyridine (90 cc) and then 3-methylbutyryl chloride (9.7 g) is added to a suspension of 2-(7-chloro-1,8-naphthyridin-2-yl)-3-hydroxy-1-isoindolinone (12.5 g) in methylene chloride (600 cc), while the temperature is maintained in the region of 25° C. After 4 hours' stirring at a temperature in the region of 25° C., 3-methylbutyryl chloride (0.7 g) is added again and the mixture is stirred for a further 16 hours at this temperature. The reaction mixture is then concentrated to dryness under reduced pressure (3 kPa) and the residue is taken up with water (500 cc). The insoluble product formed is separated by filtration, washed, dried and then recrystallized in a mixture of isopropyl ether and ethyl acetate (50:50 by volume). 2-(7-Chloro-1,8-naphthyridin-2-yl)-3-oxo-1-isoindolinyl 3-methylbutyrate (7.9 g), m.p. 154° C., is thereby obtained.

EXAMPLE 30

Pyridine (24 cc) followed, in the course of 30 minutes, by propionyl chloride (5.5 g) are added successively to a solution of 2-(7-Chloro-1,8-naphthyridin-2-yl)-3-hydroxy-1-isoindolinone (3.2 g) in methylene chloride (160 cc), while the temperature is maintained in the region of 25° C. The mixture is stirred for 3 hours at this temperature and then treated with water (100 cc). The organic phase is separated after settling has occurred, washed with water, dried and concentrated to dryness under reduced pressure (2.7 kPa). The residue obtained is crystallized in isopropyl ether and then recrystallized in a mixture of isopropyl ether and ethyl acetate (25:75 by volume). 2-(7-Chloro-1,8-naphthyridin-2-yl)-3-oxo-1-isoindolinyl propionate (1 g), m.p. 160° C., is thereby obtained.

EXAMPLE 31

The procedure is as in Example 30, but starting with 2-(7-chloro-1,8-naphthyridin-2-yl)-3-hydroxy-1-isoindolinone (6.4 g) in methylene chloride (320 cc), pyridine (48 cc) and butyryl chloride (12.8 g). After one recrystallization in isopropyl ether followed by two recrystallizations in acetonitrile, 2-(7-chloro-1,8-naphthyridin-2-yl)-3-oxo-1-isoindolinyl butyrate (3.4 g), m.p. 140° C., is obtained.

EXAMPLE 32

The procedure is as in Example 1, but starting with 3-(7-chloro-1,8-naphthyridin-2-yl)-1-isoindolinone (9.9 g) in anhydrous dimethylformamide (100 cc), 4-oxocyclohexanecarboxylic acid (4.25 g) and 1,8-diazabicyclo[5.4.0]undec-7-ene (4.6 g). After recrystallization in acetonitrile, 2-(7-chloro-1,8-naphthyridin-2-yl)-3-oxo-1-isoindolinyl 4-oxocyclohexanecarboxylate (8.5 g), m.p. 203° C., is obtained.

EXAMPLE 33

The procedure is as in Example 7, but starting with 2-(7-bromo-1,8-naphthyridin-2-yl)-3-hydroxy-1-isoindolinone (8.55 g) in methylene chloride (110 cc), triethylamine (11.1 g), 5-methylhexanoyl chloride (7 g) and 4-dimethylaminopyridine (50 mg). After the residue obtained has been crystallized in hexane and then recrystallized in ethanol, 2-(7-bromo-1,8-naphthyridin-2-yl)-3-oxo-1-isoindolinyl 5-methylhexanoate (7.5 g), m.p. 136° C., is obtained.

2-(7-Bromo-1,8-naphthyridin-2-yl)-3-hydroxy-1-isoindolinone may be prepared as described in Belgian Patent No. 815,019.

EXAMPLE 34

The procedure is as in Example 7, but starting with 5-hydroxy-6-(7-chloro-1,8-naphthyridin-2-yl)-7-oxo-6,7-dihydro-5H-pyrrolo[3,4-b]pyrazine (6.3 g) in methylene chloride (80 cc), triethylamine (5.05 g), methacryloyl chloride (3.14 g) and 4-dimethylaminopyridine (50 mg). The residue obtained is purified by recrystallization in acetonitrile followed by chromatography on neutral alumina (50 g) contained in a column 1.5 cm in diameter, eluting with methylene chloride and collecting 15-cc fractions. Fractions 12 to 34 are combined and concentrated to dryness under reduced pressure (2.7 kPa) at 40° C. 6-(7-Chloro-1,8-naphthyridin-2yl)-7-oxo-6,7-dihydro-5H-pyrrolo [3,4-b]-pyrazin-5yl methacrylate (1.4 g), m.p. 255° C., is thereby obtained.

5-Hydroxy-6-(7-chloro-1,8-naphthyridin-2-yl)-7-oxo-6,7-dihydro-5H-pyrrolo[3,4-b]pyrazine may be prepared as described in Belgian Patent No. 815,019.

EXAMPLE 35

The procedure is as in Example 7, but starting with 5-hydroxy-6-(7-chloro-1,8-naphthyridin-2-yl)-7-oxo-6,7-dihydro-5H-pyrrolo[3,4-b]pyrazine (6.3 g) in methylene chloride (80 cc), triethylamine (5.05 g), isobutyryl chloride (4.25 g) and 4-dimethylaminopyridine (50 mg). The solid obtained is washed with tetrahydrofuran. 6-(7-Chloro-1,8-naphthyridin-2-yl)-7-oxo-6,7-dihydro-5H-pyrrolo[3,4-b]pyrazin-5-yl isobutyrate (2.3 g), m.p. 260°–262° C., is thereby obtained.

5-Hydroxy-6-(7-chloro-1,8-naphthyridin-2-yl)-7-oxo-6,7-dihydro-5H-pyrrolo[3,4-b]pyrazine may be prepared as described in Belgian Patent No. 815,019.

EXAMPLE 36

An oily suspension (50% by weight; 0.96 g) of sodium hydride is added in the course of 15 minutes to a suspension of 3-hydroxy-2-(7-methoxy-1,8-naphthyridin-2-yl)-1-isoindolinone (6.15 g) in anhydrous dimethylformamide (50 cc) while the temperature is maintained in the region of 0° C., the mixture then being stirred again for 30 minutes at 0° C. Diethyl chlorophosphate (2.9 cc) is then added dropwise in the course of 30 minutes while the temperature is maintained in the region of 0° C. A solution of sodium 4-acetylaminobutanoate, prepared from 4-acetamidobutyric acid (2.9 g) in anhydrous dimethylformamide (30 cc) and an oily suspension (50% by weight; 0.96 g) of sodium hydride, is added at a temperature in the region of 0° C. to the solution obtained. The mixture is stirred for 1 hour at 0° C., then 20 hours at a temperature in the region of 20° C., and finally 4 hours at 80° C. The reaction mixture is poured into water (400 cc) and extracted with methylene chloride (3×200 cc). The organic extracts are combined and washed with water, dried and concentrated to dryness under reduced pressure (2.7 kPa). The residue obtained is purified by chromatography on silica (0.063-0.2 mm; 350 g) contained in a column 5 cm in diameter [eluant: methylene chloride/methanol (99:1 by volume)], collecting 100-cc fractions. Fractions 23 to 39 are combined and concentrated to dryness under reduced pressure (2.7 kPa) at 40° C.; the residue is recrystallized in acetonitrile. 2-(7-Methoxy-1,8-naphthyridin-2-yl)-3-oxo-1-isoindolinyl 4-acetylaminobutyrate (2 g), m.p. 190° C., is thereby obtained.

EXAMPLE 37

The procedure is as in example 7, but starting with 2-(7-methyl-1,8-naphthyridin-2-yl)-3-hydroxy-1-isoindolinone (3.7 g), 5-methylhexanoyl chloride (7.8 g), triethylamine (12 cc) and 4-diemthylaminopyridine (50 mg). After the solid obtained after treatment has been recrystallized in methylcyclohexane, 2-(7-methyl-1,8-naphthyridin-2-yl)-3-oxo-1-isoindolinyl 5-methylhexanoate (3.8 g), m.p. 144° C., is obtained.

3-Hydroxy-2-(7-methyl-1,8-naphthyridin-2-yl)-1-isoindolinone may be prepared by the method described in German Patent No. 2,423,650.

5-Methylhexanoyl chloride may be prepared by the method described by GOERNER G. L. et al., J. Org. Chem., 24, 1561 (1959).

EXAMPLE 38

The procedure is as in Example 1, but starting with 3-chloro-2-(7-chloro-1,8-naphthyridin-2-yl)-1-isoindolinone (9.9 g) in anhydrous dimethylformamide (100 cc), 4-(N-methylacetamido)butanoic acid (4.8 g) and 1,8-diazabicyclo[5.4.0]undec-7-ene (4.6 g). The oily residue obtained is purified by chromatography on silica (0.063-0.2 mm; 150 g) contained in a column 3 cm in diameter [eluant: methylene chloride/methanol (99:1 by volume)] and collecting 30-cc fractions. Fractions 76 to 175 are concentrated to dryness under reduced pressure (2.7 kPa) at 60° C. and, after crystallization in ethyl ether, 2-(7-chloro-1,8-naphthyridin-2-yl)-3-oxo-1-isoindolinyl 4-(N-methylacetamido)butyrate (3.1 g), m.p. 170° C., is obtained.

4-(N-Methylacetamido)butanoic acid may be prepared in the following manner: acetyl chloride (11.8 g) is added in the course of 1 hour to a solution, maintained at a temperature in the region of 5° C., of 4-(N-methylamino)butanoic acid hydrochloride (15.4 g) in 2.5N aqueous sodium hydroxide solution (200 cc). The mixture is stirred again for 30 minutes at approximately 5° C. and then acidified to a pH in the region of 1 using 12N aqueous hydrochloric acid solution. The mixture is concentrated to dryness at 80° C. under reduced pressure (2.7 kPa) and the residue obtained is taken up with ethanol (150 cc). A solid is separated by filtration, the filtrate is concentrated to dryness at 60° C. under reduced pressure and the residue is then taken up with methylene chloride (150 cc). The organic phase is dried over magnesium sulphate and concentrated to dryness at 60° C. under reduced pressure (2.7 kPa). 4-(N-Methylacetamido)butanoic acid (19 g) is thereby obtained in the form of an oil, which is employed in the crude state in the subsequent syntheses.

EXAMPLE 39

The procedure is as in Example 7, but starting with 2-(7-fluoro-1,8-naphthyridin-2yl)-3-hydroxy-1-isoindolinone (5 g) in methylene chloride (60 cc), triethylamine (6.5 g), 4-methylpentanoyl chloride (3.66 g) and 4-dimethylaminopyridine (10 mg). After recrystallization in ethanol, 2-(7-fluoro-1,8-naphthyridin-2-yl)-3-oxo-1-isoindolinyl 4-methylpentanoate (1.2 g), m.p. 154° C., is obtained.

2-(7-Fluoro-1,8-naphthyridin-2-yl)-3-hydroxy-1-isoindolinone may be prepared in the following manner: potassium borohydride (2.3 g) is added in small portions at a temperature in the region of 20° C. to a suspension of 2-(7-fluoro-1,8-naphthyridin-2-yl)-1,3-isoindolinedione (16.6 g) in a mixture of anhydrous methanol (90 cc) and dioxane (90 cc), and the suspension obtained is stirred for 3 hours at a temperature in the region of 20° C. The reaction mixture is then poured into a mixture of ice (120 g) and water (240 cc). The insoluble product is separated by filtration, washed with water (3×50 cc), dried in the air and recrystallized in acetonitrile. 2-(7-Fluoro-1,8-naphthyridin-2-yl)-3-hydroxy-1-isoindolinone (10.3 g), m.p. 246° C., is thereby obtained.

2-(7-Fluoro-1,8-naphthyridin-2-yl)-1,3-isoindolinedione may be prepared in the following manner: potassium fluoride (15 g) is added to a suspension, maintained under an argon atmosphere, of 2-(7-chloro-1,8-naphthyridin-2-yl)-1,3-isoindolinedione (20.6 g) in anhydrous nitrobenzene (270 cc), and the reaction mixture is heated to reflux with stirring for 22 hours. After being cooled to a temperature in the region of 80° C., the reaction mixture is concentrated to dryness under reduced pressure (0.13 kPa) at 80° C. The residue obtained is taken up with ethyl acetate (170 cc). The insoluble product is separated by filtration, washed successively with ethyl acetate (30 cc) and water (6×30 cc) and dried in the air. 2-(7-Fluoro-1,8-naphthyridin-2-yl)-1,3-isoindolinedione (16.9 g), m.p. 264° C., is thereby obtained.

2-(7-Chloro-1,8-naphthyridin-2-yl)-1,3-isoindolinedione may be prepared by the method described in Belgian Patent No. 835,325.

EXAMPLE 40

A solution of 2-(7-chloro-1,8-naphthyridin-2-yl)-3-oxo-1-isoindolinyl 4-acetamido-butyrate (25 mg) in a mixture of hexane and ethanol (50:50 by volume, 10 cc) was chromatographed on a stationary phase consisting of cellulose(trisphenylcarbamate) adsorbed on macroporous silica in a column 2.2 cm in diameter and 25 cm long. Elution was effected with a mixture of hexane and ethanol (50:50 by volume) and was followed by monitoring UV absorption of the eluate at 360 nm. The rate of flow was 9 cc a minute. The levorotatory taotary isomer was eluted at the end of 20 minutes, followed by the dextrorotatory isomer. The corresponding eluates were concentrated to dryness under reduced pressure (2.7 kPa) at 45° C. In this way (−)-2-(7 chloro-1,8-naphthyridin-2-yl)-3-oxo-1-isoindolinyl 4-acetamido-butyrate (8 mg, m.p. 199° C.) was obtained together with (+)-2-(7-chloro-1,8-naphthyridin-2-yl)-3-oxo-1-isoindolinyl 4-acetamido-butyrate (7 mg, m.p. 200° C.).

Racemic 2-(7-chloro-1,8-naphthyridin-2-yl) 3 oxo-1-isoindolinyl 4-acetamido butyrate was prepared in the manner described in Example 12.

EXAMPLE 41

Proceeding as in Example 40, but starting from 2-(7-chloro-1,8-naphthyridin-2-yl)-3-oxo-1-isoindolinyl 4-propionamido-butyrate (25 mg), (−)-2-(7-chloro-1,8-naphthyridin-2-yl)-3-oxo-1-isoindolinyl 4-proionamidobutyrate (8 mg, m.p. 205° C.) and (+)-7-chloro-1,8-naphthyridin-2-yl)-3-oxo-1-isoindolinyl 4-propionamidobutyrate (8 mg, m.p. 204° C.) were obtained.

Racemic 2-(7-chloro-1,8-naphthyridin-2-yl)-3-oxo-1-isoindolinyl 4-propionamido-butyrate was prepared as described in Example 21.

The present invention also relates to the medicinal products which contain the products of formula (I) in the pure state or in the form of compositions in which they are combined with an adjuvant, a diluant and/or a coating which is compatible and pharmaceutically acceptable. These medicinal products may be used orally, rectally, parenterally or percutaneously.

As solid compositions for oral administration, tablets, pills, powders (generally in gelatin capsules) or granules may be used. In these compositions, the active product according to the invention is mixed with one or more of inert diluants such as sucrose, lactose or starch. These compositions can also contain substances other than diluants, e.g. a lubricant such as magnesium stearate.

As liquid compositions for oral administration, emulsions that are pharmaceutically acceptable, solutions, suspension, syrups and elixirs containing inert diluants, such as water of liquid paraffin, may be used. These compositions can also contain substances other than diluants, e.g. wetting, sweetening or flavoring products.

These compositions according to the invention for parenteral administration can be suspensions, emulsions or aqueous or non-aqueous sterile solutions. As a solvent or vehicle, it is possible to use propylene glycol, a polyethylene glycol, vegetable oils, especially olive oil, or injectable organic esters, e.g. ethyl oleate. These compositions can also contain adjuvants, especially wetting agents, emulsifiers and dispersants. The sterilization may be carried out in several ways, e.g. using a bacteriological filter, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories which can contain, in addition to the active product, excipients such as cocoabutter or suppo-wax.

the compositions for percutaneous administration are creams, ointments, lotions and liniments, in which the active product is combined with liquid or pasty excipients, preferably in combination with a vehicle which promotes percutaneous migration.

The medicinal products and compositions according to the invention are especially useful in human therapy on account of their anxiolytic, hypnotic, anticonvulsant, antiepileptic and muscle relaxant action.

In human therapy, the doses depend on the effect sought and the period of treatment; they are generally between 10 and 500 mg per day orally for an adult.

In general, the doctor will determine the dosage which he considers most suitable in relation to the age and weight and all other factors particular to the subject to be treated.

The examples which follow, given without implied limitation, illustrate a composition according to the invention.

EXAMPLE A

Tablets containing 10-mg doses of active product and having the following composition are prepared according to the usual technique:

| | |
|---|---|
| 2-(7-chloro-1,8-naphthyridin-2-yl)-1-oxo-1-isoindolinyl 3-dimethylaminopropionate | 0.010 g |
| starch | 0.200 g |
| precipitated silica | 0.036 g |
| magnesium stearate | 0.004 g |

Working in the same manner, tablets may be prepared in which the active principle consists of the following products:

(RS)-2-(7chloro-1,8-naphthyridin-2-yl)-3-oxo-1-isoindolinyl 4-acetamidobutyrate (RS)-2-(7-Chloro-1,8-naphthyridin-2-yl)-3-oxo-1-isoindolinyl 1-propionyl-4-piperidinecarboxylate (RS)-2-(7-Methoxy-1,8-naphthyridin-2-yl)-3-oxo-1-isoindolinyl 5-methylhexanoate (RS)-2-(7-Chloro-1,8-naphthyridin-2-yl)-3-oxo-1-isoindolinyl 3-diisopropylaminopropionate.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of the formula:

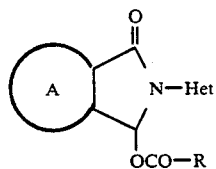

(I)

in which A forms with the pyrrole ring an isoindoline, Het denotes a naphthyridinyl radical which is unsubstituted or substituted with a halogen atom or (1 to 4 C) alkyloxy radical and R denotes an alkyl radical which is unsubstituted or substituted by alkyloxy dialkylamino, alkylcarbonylamino, piperidyl, piperidino, piperidinocarbonyl or R is a 3- or 4-piperidyl, the aforesaid alkyl radicals having a straight- or branched-chain and containing, except where specifically stated, 1 to 10 carbon atoms each, and the said piperidino and piperidyl, radicals being unsubstituted or substituted at any position by alkyl as alkylcarbonyl, or where it exists, a pharmaceutically acceptable salt or optical isomer of the said pyrrole derivative of formula (I).

2. A compound according to claim 1 in which A forms with the pyrrole ring an isoindoline, Het denotes a 1,8-naphthyridin-2-yl radical substituted with a halogen atom or a (1 to 4 C) alkyloxy radical, and R denotes a straight- or branched chain alkyl radical of 1 to 6 carbon atoms which is unsubstituted or substituted by alkyloxy, dialkylamino, alkylcarbonylamino, piperidino, piperidinocarbonyl or phenyl, or R denotes 2-pyrrolidinyl or 3- or 4-piperidyl, the said alkyl radicals being straight- or branched chain and containing, except where specifically stated, 1 to 10 carbon atoms each, and the said piperidino, piperidyl and pyrrolidinyl radicals being unsubstituted or substituted at any position by one or more alkyl or alkylcarbonyl radicals, or form a lactam group with the nitrogen atom of the ring.

3. A pharmaceutical composition which contains in combination with one or more diluents which are compatible and pharmaceutical acceptable, at least one compound formula:

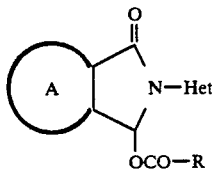

(I)

in which A forms with the pyrrole ring an isoindoline, Het denotes a naphthyridinyl radical which is unsubstituted or substituted with a halogen atom or a (1 to 4 C) alkyloxy radical and R denotes an alkyl radical which is unsubstituted or substituted by alkyloxy, dialkylamino, alkylcarbonylamino, piperidinocarbonyl, or R denotes 3- or 4-piperidyl, the aforesaid alkyl radicals having a straight- or branched chain and containing, except where specifically stated, 1 to 10 carbon atoms each, and the said piperidino and piperidyl radicals being unsubstituted or substituted at any position by alkyl or alkylcarbonyl or, where it exists, a pharmaceutically acceptable salt or optical isomer of the said compound of formula (I).

4. A pharmaceutical composition which contains in combination with one or more diluents which are compatible and pharmaceutically acceptable, at least one compound formula:

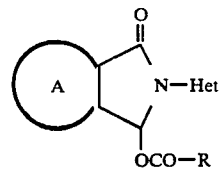

(I)

in which A forms with the pyrrole ring an isoindoline, Het denotes a naphthyridinyl, pyridyl or quinolyl radical which is unsubstituted or substituted with a halogen atom or a (1 to 4 C) alkyl, (1 to 4 C) alkyloxy, (1 to 4 C) alkylthio or trifluoromethyl radical and R denotes a straight- or branched-chain alkenyl radical containing 3 to 19 carbon atoms or R denotes an alkyl radical which is unsubstituted or substituted by alkyloxy, alkylthio, cycloalkyl of 3 to 6 carbon atoms, amino, alkylamino, dialkylamino, alkylcarbonylamino (in which the amino portion can optionally be substituted by alkyl), piperidyl, piperidino, carbamoyl, alkyl-carbamoyl, dialkyl-carbamoyl, piperidinocarbonyl, phenyl, pyridyl or 1-imidazolyl, or R denotes 2- or 3-pyrrolidinyl or 2-, 3- or 4-piperidyl, the aforesaid alkyl radicals having a straight- or branched chain and containing, except where specifically stated, 1 to 10 carbon atoms each, and the said piperidino, piperidyl, and pyrrolidinyl radicals being unsubstituted or substituted at any position by alkyl, alkylcarbonyl, benzyl or hydroxyalkyl, or form a lactam group with the nitrogen atom of the ring, or, where it exists, a pharmaceutically acceptable salt or optical isomer of the said compound of formula (I).

5. A compound according to claim 1 which is (RS)-2-(7-chloro-1,8-naphthyridin-2-yl)-3-oxo-1-isoindolinyl 4-acetamidobutyrate and its (+) and (−) enantiomers.

6. A compound according to claim 1 which is (RS)-2-(7-chloro-1,8-naphthyridin-2-yl)-3-oxo-1-isoindolinyl 1-propionyl-4-piperidinecarboxylate.

7. A compound according to claim 1 which is (RS)-2-(7-chloro-1,8-naphthyridin-2-yl)-3-oxo-1-isoindolinyl 5-methylhexanoate.

8. A compound according to claim 1 which is (RS)-2-(7-chloro-1,8-naphthyridin-2-yl)-3-oxo-1-isoindolinyl 3-diisopropylaminopropionate.

9. Method for producing an anxiolytic, hypnotic, anti-convulsant, anti-epileptic, or myorelaxant therapeutic effect in a subject in need of such therapy which comprises administering to such subject an effective amount of a compound as claimed in claim 1.

* * * * *